US006375943B1

(12) United States Patent
Raw et al.

(10) Patent No.: US 6,375,943 B1
(45) Date of Patent: Apr. 23, 2002

(54) ATTRACTANT FOR THE MEDITERRANEAN FRUIT FLY, THE METHOD OF PREPARATION AND METHOD OF USE

(75) Inventors: Andre S. Raw, Columbia, MD (US); Eric B. Jang, Hilo, HI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/526,334

(22) Filed: Mar. 15, 2000

Related U.S. Application Data

(60) Provisional application No. 60/176,192, filed on Jan. 14, 2000.

(51) Int. Cl.$^7$ .......................... A01N 37/00; A01N 37/08; C07C 69/75
(52) U.S. Cl. .......................... 424/84; 514/529; 560/125
(58) Field of Search ........................... 424/84; 514/529; 560/125

(56) References Cited

U.S. PATENT DOCUMENTS

| | | | |
|---|---|---|---|
| 3,016,329 A | 1/1962 | Beroza et al. ................. | 167/48 |
| 4,152,422 A | 5/1979 | Ohinata et al. ................ | 424/84 |
| 4,764,366 A | 8/1988 | McGovern et al. ........... | 424/84 |
| 4,891,217 A | 1/1990 | McGovern et al. ........... | 424/84 |

OTHER PUBLICATIONS

Avery, J.W., et al., "Use of Ceralure and Trimedlure in Mediterranean Fruit Fly (Diptera: Tephritidae) Mass–Trapping Tests", *J. Entomol. Sci.*, vol. 29(4), pp. 543–556, Oct., 1994.
Avery, J.W., et al., "Regioselective Synthesis of Ceralure B$_1$ and A, Ethyl cis–(and trans–) 5–Iodo–trans–2–Methylcyclohexane–1–Carboxylate", *Tetrahedron Letters*, vol. 35(50), pp. 9337–9338, 1994.
Beroza, M., et al., "New Attractants for the Mediterranean Fruit Fly", *Agriculture and Food Chemistry*, vol. 9(5), pp. 361–365, Sep.–Oct., 1961.
Clive, D.L.J., et al.,"Total Synthesis of Both(+)–Compactin and (+)–Mevinolin. General Strategy Based on the Use of a Special Titanium Reagent for Dicarbonyl Coupling", *J. Am. Chem. Soc.*, vol. 112(8), pp. 3018–3028, 1990.
Corey, E.J., et al., "Pyridinium Chlorochromate. An Efficient Reagent for Oxidation of Primary and Secondary Alcohols to Carbonyl Compounds", *Tetrahedron Letters*, No. 31, pp. 2647–2650, Jun. 10, 1975.
DeMilo, A.B., et al. "Trimedlure: Effects of Structural Modifications on Its Attractiveness to Mediterranean Fruit Fly Males (Diptera: Tephritidae)",*J. Economic Entomology*, vol. 87(6), 1494–1501, Dec., 1994.
DeMilo, A.B., et al., "Structure Confirmation of the Four trans Isomers of Ceralure, A Medfly Attractant, by NMR",*J. Agric. Food Chem.*, vol. 42(10), pp. 2089–2093, 1994.

DeMilo, A.B., et al., "Capillary Gas Chromatography Method for the Analysis of the trans isomers of Ceralure, a Medfly Attractant", *J. Chromatography A*, vol. 673, pp. 295–298, 1994.
Doolittle, R.E., "Trimedlure Enantiomers: Differences in Attraction for Mediterranean Fruit Fly, Ceratitis capitata (WIED.) (Diptera: Tephritidae)", *J. Chemical Ecology*, vol. 17(2), pp. 475–484, 1991.
Evans, D.A., et al., "Contrasteric Carboximide Hydrolysis with Lithium Hydroperoxide", *Tetrahedron Letters*, vol. 28(49), pp. 6141–6144, 1987.
Evans, D.A., et al., "Asymmetric Diels–Alder Cycloaddition Reactions with Chiral α,β–Unsaturated N–Acyloxolidinones", *J. Am. Chem. Soc.*, vol. 110(4), pp. 1238–1256, 1988.
Garegg, J., et al., "Novel Reagent System for Converting a Hydroxy–group into an Iodo–group in Carbohydrates with Inversion of Configuraton", *J.C.S. Chem. Comm.*, pp. 978–980, 1979.
Harris, E.J., et al., "Sticky Traps for Detection and Survey of Three Tephritids",*J. Economic Entomology*, vol. 64(1), pp. 62–65, Feb., 1971.
House, H.O., et al., "Enones with Strained Double Bonds. 8. The Bicyclo[3.2.1]octane Systems", *J. Org. Chem.*, vol. 48(10), pp. 1643–1654, 1983.
Jackson, D.S., et al., "Medfly in California 1980–1982", *Bulletin of the ESA*, pp. 29–37, Winter, 1985.
Knapp, S., et al., "Synthesis and Reactions of Iodo Lactams", *J. Org. Chem.*, vol. 53(17), pp. 4006–4014, 1988.
Leonhardt, B.A., et al., "Comparison of Ceralure and Trimedlure Attractants for the Male Mediterranean Fruit Fly (Diptera:Tephritidae)", *J. Entomol. Sci.*, vol. 31(2), pp. 183–190, 1996.
Leonhardt, B.A., et al., "Design, Effectiveness, and Performance Criteria of Dispenser Formulations of Trimedlure, an Attractant of the Mediterranean Fruit Fly (Diptera: Tephritidae)", *J. Economic Entomology*, vol. 82(3), pp. 860–867, Jun., 1989.

(List continued on next page.)

*Primary Examiner*—John Pak
(74) *Attorney, Agent, or Firm*—M. Howard Silverstein; John D. Fado; G. Byron Stover

(57) ABSTRACT

A method of attracting the Mediterranean fruit fly by subjecting the Mediterranean fruit fly to an attractant, wherein the attractant is ethyl (1R,2R,5R)-5-iodo-2-methylcyclohexane-1-carboxylate in an enantomeric excess of at least 70% and a regio- and diastereochemical purity of >5:1. The compound ethyl (1R,2R,5R)-5-iodo-2-methylcyclohexane-1-carboxylate, in an enantomeric excess of at least 70% and a regio- and diastereochemical purity of >5:1, may be stereoselectively synthesized on a multigram scale in 15% yield by reacting ethyl (1R,2R,5S)-5-hydroxy-2-methyl-1-carboxylate with Ph$_3$P-imidazole-I$_2$ (or Ph$_3$P-2,6-lutidine-I$_2$) in a carbon tetrachloride/methlylene chloride mixture. The 1R,2R,5R enantiomer is significantly more attractive than its enantiomeric counterpart (1S,2S,5S), or either of the commercial products trimedlure or ceralure, each a mixture of 16 regio and stereoisomers.

11 Claims, 2 Drawing Sheets

OTHER PUBLICATIONS

Leonhardt, B.A., et al., "Performance of Controlled-Release Formulations of Trimedlure to Attract the Mediterranean Fruit Fly, *Ceratitis capitata*", *Entomol. exp. Appl.*, vol. 44, pp. 45–51, 1987.

McGovern, T.P., et al., "Relative Attraction of the Mediterranean Fruit Fly (Diptera: Tephritidae) to the Eight Isomers of Trimedlure", *J. Economic Entomology*, vol. 83(4), pp. 1350–1354, Aug., 1990.

McGovern, T.P., et al., "Attractiveness of trans–Trimedlure and its four Isomers in Field Tests with the Mediterranean Fruit Fly (Diptera: Tephritidae)", *J. Economic Entomology*, vol. 80(3), pp. 617–620, Jun., 1987.

Sonnet, P.E., et al., "Enantiomers of the Biologically Active Components of the Insect Attractant Trimedlure", *J. Org. Chem.*, vol. 49(24), pp. 4639–4643, 1984.

Thom, C., et al., A Practical Synthesis of (R)–(+)–Cyclohex–3–enecarboxylic Acid via an Asymmetric Diels–Alder Reaction, *Synthesis*, pp. 475–477, May, 1993.

Warthen, J.D., et al., "Trans–Ceralure Isomers: Difference in Attraction for Mediterranean Fruit Fly, *Ceratitis capitata* (WIED) (Diptera: Tephritida)", *J. Chemical Ecology*, vol. 20(3), pp. 569–578, 1994.

Warthen, J.D., et al., "Comparison of Ceralure and Trimedlure Controlled–Release Formulations for Male Mediterranean Fruit Flies in C&C Traps", *J. Chemical Ecology*, vol. 24(8), pp. 1305–1314, 1998.

Warthen, J.D., et al., "Attractancy Evaluation of Ceralure–B1 Isomer via Field Captures of Mediterranean Fruit Flies (Diptera: Tephritidae)", *J. Environ. Sci. Health, B*, vol. 34(2), pp. 333–347, 1999.

Tanaka, N., et al., "Low–Cost Larval Rearing Medium for Mass Production of Oriental and Mediterranean Fruit Flies", *J.Economic Entomology*, vol. 62(4), pp. 967–968, Aug., 1969.

Avery, J.W., et al., "Relative Attractancy of Ceralure and Trimedlure for Mediterranean Fruit Fly (*Ceratitis capitata*)", Abstract No. 95(Date Unavailable).

Raw, Andre S. et al., "Enantioselective synthesis of Ceralure B1 . . . " Tetrahedron, vol. 56(21), 2000, pp. 3285–3290.*

* cited by examiner

ATTRACTANT FOR THE MEDITERRANEAN FRUIT FLY, THE METHOD OF PREPARATION AND METHOD OF USE This application claims the benefit of U.S. Provisional Application No. 60/176,192, filed Jan. 14, 2000, which is incorporated herein by reference in its entirety.

BACKGROUND OF THE INVENTION

This invention relates to a method of attracting the Mediterranean fruit fly by subjecting the Mediterranean fruit fly to an attractant, wherein the attractant is ethyl (1R,2R,5R)-5-iodo-2-methylcyclohexane-1-carboxylate in an enantiomeric excess of at least 70% and a regio and diastereo chemical purity of >5:1. The compound ethyl (1R,2R,5R)-5-iodo-2-methyl cyclohexane-1-carboxylate, in an enantomeric excess of at least 70% and a regio and diastereochemical purity of >5:1, may be prepared by reacting ethyl (1R,2R,5S)-5-hydroxy-2-methyl-1-carboxylate with $Ph_3P$-imidazole-$I_2$ (or $Ph_3P$-2,6-lutidine-$I_2$) in a carbon tetrachloride/methlylene chloride mixture.

The Mediterranean fruit fly, *Ceratitas capitata* (Wiedemann) commonly known as the medfly, is a worldwide pest that feeds on 253 fruits and vegetables (Liquido, N. J., et al., Misc. Publ. Entomol. Soc. Am., 77:1 (1991)). The establishment of this exotic pest into the continental United States would significantly increase pesticide use and curtail fruit and vegetable exports, a multi-billion dollar industry (Jackson, D. S., et al., Entomol. Soc. Am., 31:2937 (1985)). For more than 30 years trimedlure (TML), a mixture of sixteen regio- and stereoisomers of tert-butyl esters of 4 (and 5)-chloro-2-methylcyclohexane-1-carboxylate (1), has been widely used as an attractant in traps used to monitor and detect male medfly (Beroza, M., et al., J. Agric. Food Chem., 9: 361–365 (1961)). The commercial trimedlure is formulated in a polymeric plug-type dispenser containing 2 g of trimedlure which acts as a controlled release dispenser for up to 8 weeks in Jackson traps (Leonhardt, B. A., et al., J. Econ. Entomol., 82: 860–867 (1989); Leonhardt, B. A., et al., Entomol. Exp. Appl., 44: 45–51 (1987)). HPLC separation of these sixteen regio- and stereoisomers of tert-butyl esters of 4 (and 5)-chloro-2-methylcyclohexane-1-carboxylate (1) made possible a field study of the relative attractiveness of these racemates toward the Mediterranean fruit fly (McGovern, T. P., et al., J. Econ. Entomol., 83:1350–1354 (1990)). Of these stereoisomers, TML-C (2) was shown to be most active. Particularly noteworthy is the ability of the medfly to discriminate among the two enantiomers of TML-C, with the (1S, 2S, 4R) configuration being most attractive (Sonnet, P. E., et al., J. Org. Chem., 49: 4639–4643 (1984); Doolittle, R. E., et al., J. Chem. Ecol., 17: 475–484 (1991)).

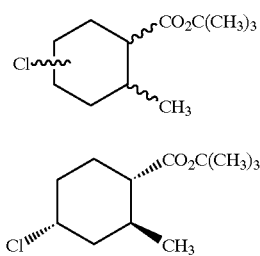

Recently, an iodo analog of trimedlure, ceralure (CER) (3), a mixture of 16 regio- and stereoisomers of ethyl 4 (and 5)-iodo-2-methylcyclohexane-1-carboxylate, has been found to be a more persistent and potent attractant than TML (U.S. Pat. No. 4,764,366). A field study designed to measure the relative attractiveness of these racemates, which were tediously separated by HPLC, demonstrated that ethyl cis-5-iodo-trans-2-methylcyclohexane-1-carboxylate (CER $B_1$) (4) is most active (Warthen, J. D., J. Chem. Ecol, 20: 569–578 (1994)).

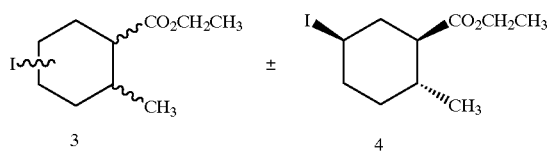

SUMMARY OF THE INVENTION

We have discovered that ethyl (1R,2R,5R)-5-iodo-2-methylcyclohexane-1-carboxylate, in an enantomeric excess of at least 70% and a regio- and diastereochemical purity of >5:1, may be prepared by reacting ethyl (1R,2R,5S)-5-hydroxy-2-methyl-1-carboxylate with $Ph_3P$-imidazole-$I_2$ (or $Ph_3P$-2,6-lutidine-$I_2$) in a carbon tetrachloride/methlylene chloride mixture.

In accordance with this discovery, it is an object of the invention to provide ethyl (1R,2R,5R)-5-iodo-2-methylcyclohexane-1-carboxylate in an enantomeric excess of at least 70% and a regio- and diastereochemical purity of >5:1.

It is another object of the invention to provide a composition for attracting the Mediterranean fruit fly wherein the composition contains ethyl (1R,2R,5R)-5-iodo-2-methylcyclohexane-1-carboxylate in an enantomeric excess of at least 70% and a regio- and diastereochemical purity of >5:1.

It is also another object of the invention to provide a method of attracting the Mediterranean fruit fly by subjecting the Mediterranean fruit fly to an attractant, wherein the attractant is ethyl (1R,2R,5R)-5-iodo-2-methylcyclohexane-1-carboxylate in an enantomeric excess of at least 70% and a regio- and diastereochemical purity of >5:1.

DETAILED DESCRIPTION OF THE INVENTION

Figure 1:
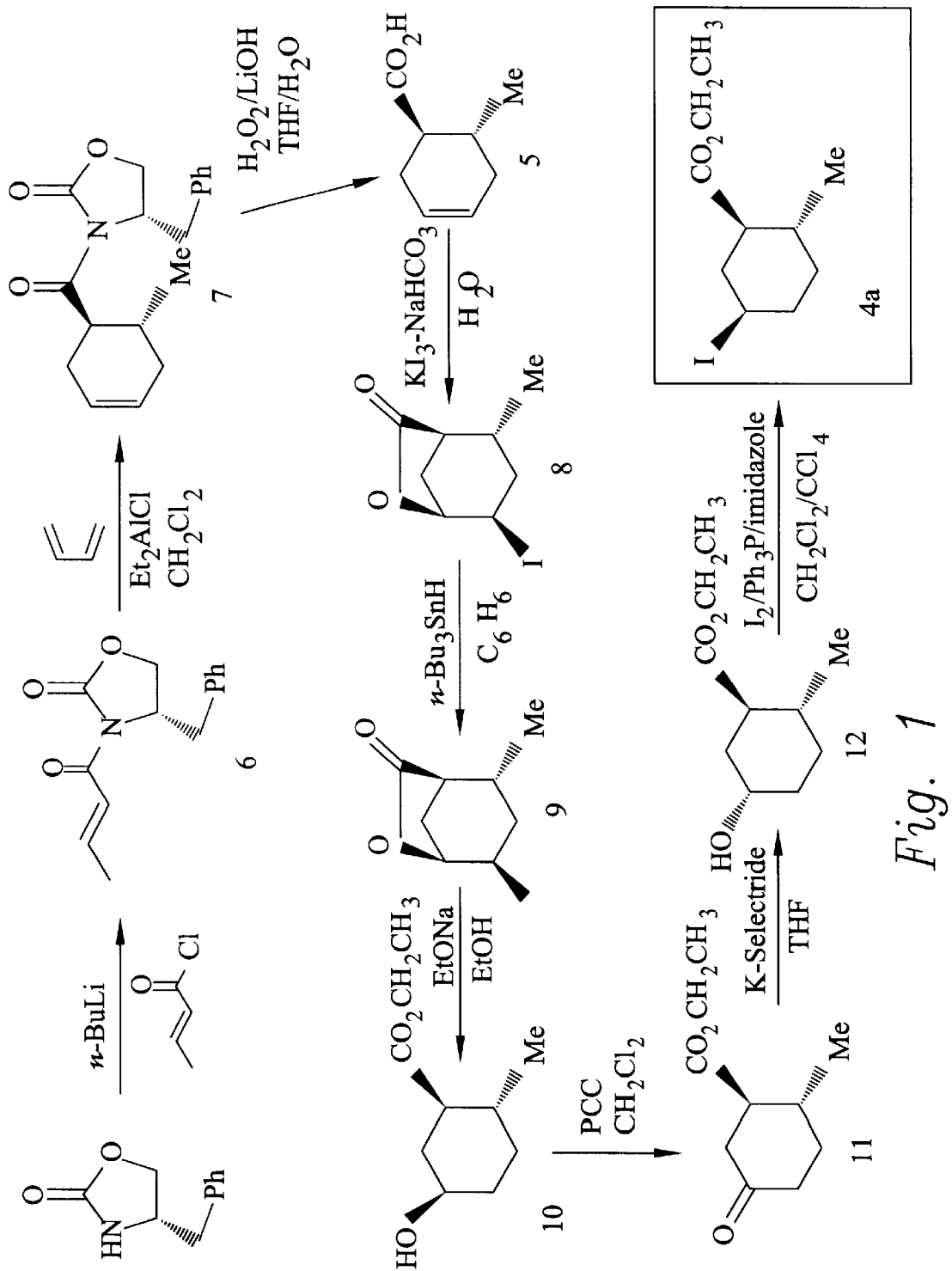
FIG. 1 shows a scheme for the enatioselective synthesis of ethyl (1R,2R,5R)-5-iodo-2-methylcyclohexane-1-carboxylate (CER $B_1$)

The present invention provides an efficient enantioselective synthesis of CER $B_1$ which is amenable to multigram scale. Our synthetic plan for developing an enantioselective synthesis of 4 is shown in FIG. 1. We sought to utilize an asymmetric Diels-Alder reaction to obtain the enantiomers of sigluric acid 5. This would avoid the tedious multistep chiral resolution of 5, used previously for the synthesis of the enantiomers of TML (Doolittle, R. E., et al., J. Chem. Ecol., 17: 475–484 (1991)). Evans has described the asymmetric Diels-Alder technique with chiral α,β-unsaturated N-acyloxazolidinones (Evans, D. A., J. Am. Chem. Soc., 110: 1238–1256 (1988); Clive, D. E., et al., J. Am. Chem. Soc., 112: 3018–3028 (1990)). Most appealing is the ready availability of both enantiomers of the benzyloxazolidinone chiral auxiliary. Hence, treatment of the chiral oxazolidinone (i.e., (R)-4-(phenylmethyl)-2-oxazolidinone 5) derived from D-phenylalanine with n-butyllithium followed by addition of (E)-crotonyl chloride generated the chiral α,β-unsaturated N-acyloxazolidinone 6 in 90% yield. The asymmetric reaction of 6 with butadiene in the presence of 2.0 equivalents of the Lewis acid catalyst $Et_2$ AlCl at −15° C. generated the adduct 7 with high diastereoselectivity (ds>97:1). Galvinoxyl was employed in this procedure to prevent the polymerization of butadiene under the reaction conditions (Thom, C., Synthesis, 475–477 (1993)). Without isolation, 7 was subjected to contrasteric carboximide hydrolysis with lithium hydroperoxide (Evans, D. A., et al., Tetrahedron Lett., 28: 6141–6144 (1987)) to afford (1R,6R)-6-methyl-3-cyclohexene-1-carboxylic acid 5 in 51% overall yield from 6. The optical purity of 5 was judged to be 97% ee on a chiral cyclodextrin column. The chiral auxiliary was also recovered in 87% yield. The absolute configuration of 5 is based on precedent of analogous reactions (Evans, D. A., et al., J. Am. Chem. Soc., 110: 1238–1256 (1988)). Additionally, the literature value for the rotation of 5 ($[alpha]_D$=−84.2°) confirms the stereochemical assignment (Doolittle, R. E., et al., J. Chem. Ecol., 17: 475–484 (1991).

Iodolactonization of 5 with $I_2$, KI and $NaHCO_3$ provided 8 in a highly regioselective manner in 87% yield (House, H. O., et al., J. Org. Chem., 48: 1643–1654 (1983); Avery, J. W., et al., Tetrahedron Lett., 35: 9337–9338 (1994)). Reduction of iodolactone 8 to lactone 9 proceeded smoothly in 94% yield with n-$Bu_3$SnH in the presence of catalytic AIBN (2,2'-azobisisobutyronitrile) in refluxing benzene (House, H. O., et al., J. Org. Chem., 48: 1643–1654 (1983)); the transformation 8 to 9 may also be effected by Raney Nickel (a heterogeneous metal catalyst) in the presence of pyridine under a pressure of 50 psi of hydrogen gas, the yield is comparable to the old procedure but uses cheaper, less toxic reagents and is operationally easier. Finally, ring opening of the lactone with sodium ethoxide in ethanol generated 10 in quantitative yield (99%). Hence the synthetic sequence 5 to 10 was, in effect, equivalent to the regio- and stereoselective addition of water across the olefin. However, the configuration of the hydroxyl was opposite to that desired. Inversion of the hydroxyl was required. Mitsunobo inversion of a hydroxyl in the cyclohexane ring was plagued with difficulties, due to the propensity of elimination as well as low reactivity resulting from steric hindrance of an approaching nucleophile. In an alternate approach, the hydroxyl in 10 was oxidized with pyridinium chlorochromate (PCC)(Corey, E. J., et al., Tetrahedron Lett., 35: 2647–2650 (1975)) in methylene chloride to generate the ketone (11) in high yield (95%). Stereoselective reduction of the ketone should provide the desired alcohol 12 with inverted stereochemistry. As the cyclohexanone ring in 11 should exist in a distorted chair conformation with the ethyl ester and methyl groups occupying equatorial positions, reduction of the ketone with hydride from an equatorial trajectory should provide the desired alcohol 12 with inverted stereochemistry. Thus reduction of 11 with $NaBH_4$ gave predominantly 10 (ds=9:1) most likely as a result of approach of comparatively unhindered borohydride from the axial position. Interestingly, reduction of the ketone with the sterically encumbered reducing agent $LiAlH(OCCH_3)_3$ also gave a preponderance of 10 (ds>99:1). However, reduction of 11 with K-Selectride (potassium tri-sec-butylborohydride; Knapp, S., et al., J. Org. Chem., 53: 4006–4014 (1988)) in THF at −78° C., followed by oxidation of the trialkylborane with hydrogen peroxide under neutral conditions generated the desired axial alcohol 12 with high stereoselectivity (ds>25:1). Alcohol 12 was then isolated in pure form by simple flash chromatography (86%).

Activation of the hydroxyl, followed by nucleophilic displacement with iodide should generate the desired CER $B_1$ (4a) stereoisomer. However, this last step of the sequence proved to be very difficult. A variety of conditions were attempted, including $Ph_3$P-DEAD-$CH_3$I, $Ph_3$P-N-iodosuccinimide, $Ph_3$P-DEAD-$ZnI_2$, $I_2SiH_2$, and o-phenylene phosphochloridite-$I_2$, all of which proved unsuccessful. In those instances, starting material was recovered, along with CER $B_1$ (4a) and elimination product. Without being bound by theory, we attribute this to the steric hindrance of the axial hydroxyl in 12 for activation. If activation were to occur, facile E-2 elimination of the activated axial hydroxyl would ensue before nucleophilic attack by iodide. Other reagents, including $P_2I_4$, $Me_3$SiCl—NaI, $Cl_3$SiMe—NaI, and trimethylsilylpolyphosphate/NaI, did yield CER $B_1$ (4a), albeit in poor stereoselectivity, most likely due to the highly ionic nature of the intermediates involved. We found that $Ph_3$P-imidazole-$I_2$ (or $Ph_3$P-2,6-lutidine-$I_2$) in a 2:1 carbon tetrachloride/methylene chloride mixture at room temperature surprisingly yielded CER $B_1$ (4a) in fair yield (55%) and in high stereoselectivity (ds>50:1). Fortunately, the elimination side product was easily removed by flash chromatography. The $^1$H and $^{13}$C NMR spectra of CER $B_1$ (4a) synthesized in this manner were identical to those of an authentic racemic sample previously isolated from the mixture of CER stereoisomers by HPLC (Warthen, J. D., et al., J. Chem. Ecol., 20: 569–578 (1994)). Synthesis of optically pure CER $B_1$ (4a) by this route yielded material on a 6.0-g scale. The opposite enantiomer (4b) was also generated from the readily available benzyloxazolidinone chiral auxiliary derived from L-phenylalanine. Both enantiomers of CER $B_1$ (4) were determined to be 97% ee on a chiral GC cyclodextrin column.

Although the preparative procedures described herein are the preferred synthesis for the compounds (e.g., ethyl (1R,2R,5R)-5-iodo-2-methylcyclohexane-1-carboxylate) described herein, it is within the scope of this invention to prepare the compounds using any suitable procedure.

The ethyl (1R,2R,5R)-5-iodo-2-methylcyclohexane-1-carboxylate (4a) may be used as is or may be dissolved in volatile inert solvents such as liquid hydrocarbons, emulsified in water, or admixed with any other solid or inert liquid carrier. When used in actual practice in the field, the ethyl (1R,2R,5R)-5-iodo-2-methylcyclohexane-1-carboxylate (4a) may be impregnated on a solid carrier such as paper, cloth, sawdust, wood chips, or other absorbent materials. The ethyl (1R,2R,5R)-5-iodo-2-methylcyclohexane-1-carboxylate (4a) may also be dispersed into the atmosphere by spraying or by dipping wicks into containers holding the ethyl (1R,2R,5R)-5-iodo-2-methylcyclohexane-1-carboxylate (4a). Further, the ethyl (1R,2R,5R)-5-iodo-2-methylcyclohexane-1-carboxylate (4a) may be used in bait traps or lures usually provided with means to prevent the exit of insects so that the size and location of infestations may be ascertained or so that mass trapping and killing of male medflies is achieved.

For optimum results, the ethyl (1R,2R,5R)-5-iodo-2-methylcyclohexane-1-carboxylate (4a) should be used in a substantially pure form, that is, the ethyl (1R,2R,5R)-5-iodo-2-methylcyclohexane-1-carboxylate (4a) must be free of undesirable contaminants that tend to mask or otherwise inhibit its effectiveness as an attractant. Generally, the ethyl (1R,2R,5R)-5-iodo-2-methylcyclohexane-1-carboxylate (4a) is substantially free of ethyl (1S, 2S, 5S)-5-iodo-2-methylcyclohexane-1-carboxylate (4b), e.g., in an enantomeric excess of at least 70% or higher or at least 80% or higher, preferably at least 90% excess or higher, more preferably at least 95% excess or higher, most preferably at least 97% excess or higher. The ethyl (1R,2R,5R)-5-iodo-2-methylcyclohexane-1-carboxylate (4a) may be substantially enantiopure. Generally, the ethyl (1R,2R,5R)-5-iodo-2-methylcyclohexane-1-carboxylate (4a) produced according to the present invention has high regio- and diastereochemical purity (>5:1), as analyzed on a 60 m SPB-608 column, thus indicating that the other 14 regio- and diastereomers are present at a 5 fold lower concentration than ethyl (1R,2R,5R)-5-iodo-2-methylcyclohexane-1-carboxylate (4a); preferably the regio- and diastereochemical purity is >10:1, more preferably the regio- and diastereochemical purity is >15:1, most preferably the regio- and diastereochemical purity is >40:1.

The ethyl (1R,2R,5R)-5-iodo-2-methylcyclohexane-1-carboxylate (4a) may also be used with other medfly attractants (e.g., the 1S,2S,4R configuration of TML-C (1,1-dimethylethyl-cis-4-chloro-trans-2-methylcyclohexane-1-carboxylate)) or Mediterranean fruit fly control agents (e.g., insecticides, chemosterilants or the like). When used, these agents should be used in an amount which, as readily determined by one skilled in the arts, will not interfere with the effectiveness of ethyl (1R,2R,5R)-5-iodo-2-methylcyclohexane-1-carboxylate (4a). In addition, it is expected that good results can also be achieved when the ethyl group of the ester in (4a) is replaced by a methyl group or by 2,2,2-trifluoroethyl.

The following examples are intended only to further illustrate the invention and are not intended to limit the scope of the invention as defined by the claims.

EXAMPLES

Melting points were uncorrected. $^1$H NMR and $^{13}$C{$^1$H}NMR spectra were recorded with TMS as an internal standard in CDCl$_3$ on a Bruker QE-300 spectrometer unless otherwise stated. $^1$H NMR coupling constants are reported in Hz. Mass spectra were obtained with a Hewlett Packard 5971 GC-MS equipped with a 30 m DB-5 (J&W Scientific) fused silica column. Optical rotations were recorded using a Perkin-Elmer Model 241 automatic polarimeter operated at the sodium-D (589 nm) wavelength. Chiral gas chromatography was performed on a Shimadzu Model 14A gas chromatograph fitted with a 30 m Chiraldex DBM column using hydrogen as the carrier gas. Combustion analyses were conducted by Galbraith Laboratories, Inc., Knoxville, Tenn. Tetrahydrofuran (THF) was distilled from sodium/benzophenone; methylene chloride and benzene were distilled from CaH$_2$ and purged with nitrogen before using. Unless otherwise noted, materials were obtained from commercial suppliers and were used without further purification. All reactions were carried out under a nitrogen atmosphere.

(4R)-3-((E)-2-butenoyl)-4-(phenylmethyl)-2-oxazolidinone (6) was synthesized according to a literature procedure (Evans, D. A., et al., J. Am. Chem. Soc., 110: 1238–1256 (1988)). The product was recrystallized from ethanol to yield a white solid (156.4 g, 90%). R$_f$ 0.20 (ethyl acetate/hexane 1:9); m.p. 79–81° C.; $^1$H NMR (300 MHz, CDCl$_3$) δ 7.14–7.35 (m, 7H), 4.67–4.75 (m, 1H), 4.10–4.21 (m, 2H), 3.30 (dd, J=3.4, 13.2, 1H), 2.79 (dd, J=9.5, 13.2, 1H), 1.97 (d, J=5.7, 3H); $^{13}$C NMR (75 MHz, CDCl$_3$) δ 164.6, 153.2, 146.3, 135.2, 129.2, 128.6, 127.0, 121.7, 65.8, 54.9, 37.5, 18.2; MS (EI) m/z 245 (M$^+$, 10), 230 (11), 154 (12), 133 (4) 91 (9), 69 (100), 41 (11); [α]$_D$–78.3° (c=3.83, CHCl$_3$).

(4R)-3-((4'R,5'R)-cyclohexene-4'-carbonyl)-4-(phenylmethyl)-2-oxazolidinone (7) (Clive, D. E., et al., J. Am. Chem. Soc., 112: 3018–3028 (1990)). A 3 L, 3-neck r.b. flask equipped with a dry-ice acetone condenser was charged with oxazolidinone 6 (70.0 g, 0.286 mmol), galvinoxyl (500 mg, 1.2 mmol), and 400 mL of methylene chloride. After cooling to −78 ° C., butadiene (800 mL, 9.6 mol), dried by passage through Drierite, was condensed into the solution. Diethylaluminum chloride (0.570 mmol, 1.8 M in toluene) was added over 10 min and the solution was stirred overnight at −15° C. to −10° C. The reaction was quenched by addition to 1 M HCl (1000 mL). The layers were separated and the aqueous layer was extracted with methylene chloride (4×250 mL). The combined organics were neutralized by stirring with solid NaHCO$_3$, dried (MgSO$_4$) and the volatiles were removed in vacuo to give an oil (103.86 g, 107% crude yield). This was carried onto the next step without purification. A portion of the sample was purified by flash chromatography (silica gel, 230–400 mesh, ethyl acetate-hexane) to give a solid; R$_f$ 0.25 (ethyl acetate/hexane 1:9); m.p. 79–80° C.; $^1$H NMR (300 MHz, CDCl$_3$) δ 7.19–7.36 (m, 5H), 5.69–5.73 (m, 2H), 4.68–4.76 (m, 1H), 4.14–4.24 (m, 2H), 3.70 (dt, J=5.5, 10.2, 1H), 3.26 (dd, J=3.2, 13.5, 1H), 2.79 (dd, J=9.5, 13.5, 1H), 2.35–2.43 (m, 1H), 2.02–2.27 (m, 3H), 1.75–1.86 (m, 1H), 0.97 (d, J=6.4, 3H); $^{13}$C NMR (75 MHz, CDCl$_3$) δ 176.4, 153.1, 135.3, 129.4, 128.9, 127.3, 126.3, 124.6, 66.0, 55.3, 44.2, 37.9, 33.0, 30.3, 29.0, 19.5; MS (EI) m/z 299 (M$^+$, 13), 284 (1), 178 (25), 122 (100), 95 (46), 79 (30); [α]$_D$–141.5° (c=1.48, CHCl$_3$).

(1R, 6R)-6-methyl-3-cyclohexene-1-carboxylic acid (5) (Doolittle, R. E., et al., J. Chem. Ecol., 17: 475–484 (1991)). To a cold (0° C.) solution of 7 (103.86 g, 0.286 mol), in 4:1 THF/water (500 mL), was added 30% hydrogen peroxide (160 mL, 1.40 mol), followed by lithium hydroxide (27.4 g, 0.652 mol). The resulting mixture was slowly allowed to warm to room temperature and after 4 h the reaction was complete. The solution was cooled (0° C.) and sodium sulfite (202 g, 1.6 mole) was added. The bulk of the THF was removed in vacuo and the resulting mixture (pH 12–13) was extracted with methylene chloride (5×200 mL) to remove the chiral auxiliary. The combined methylene chloride organics were dried (MgSO$_4$) and the volatiles were removed in vacuo to yield 44.0 g (87% yield) of the recovered benzyloxazolidinone auxiliary. The aqueous layer was acidified to pH 1–2 with 12 M HCl and extracted with ethyl acetate (5×300 mL). The combined ethyl acetate extracts were dried (Na$_2$SO$_4$) and the volatiles were removed in vacuo to yield an oil which was purified by flash chromatography to give a solid (20.2 g, 51% overall yield from 6). The methyl ester of 5 was shown to be at 97% ee on a 30 m Chiraldex column. R$_f$ 0.40 (ethyl acetate/hexane 1:1); m.p. 65–66° C.; $^1$H NMR (300 MHz, CDCl$_3$) δ 10.2–11.8 (b, 1H), 5.61–5.69 (m, 2H). 2.12–2.33 (m, 4H), 1.89–2.00 (m, 1H), 1.67–1.77 (m, 1H), 1.02 (d, J=6.6, 3H); $^{13}$C NMR (75 MHz, CDCl$_3$) δ 182.3, 126.3, 124.5, 46.8, 32.9, 30.3, 28.7, 19.7; MS (EI) m/z 140 (M$^+$, 21), 122 ([M-H$_2$O]$^+$, 16), 111 (14), 95 (100), 79 (75), 67 (49); [α]$_D$–99.0° (c=4.89, CHCl$_3$).

(1R, 2R, 4S, 5S)-4-iodo-2-methyl-6-oxabicyclo[3.2.1] octan-7-one (8) (Avery, J. W., et al., Tetrahedron Lett., 35: 9337–9338 (1994)). To a solution of optically active 5 (16.8 g, 120 mmol), in methylene chloride (200 mL) and water (400 mL), was added NaHCO₃ (20.1 g, 240 mmol), KI (120 g, 0.720 mmol) and iodine (91.0 g, 0.360 mmol). The resulting mixture was protected from light and stirred for 24 h. The solution was cooled (0° C.) and sodium thiosulfate was carefully added until the dark iodine color disappeared. This was extracted with diethyl ether (4×300 mL). The combined organics were dried (MgSO₄) and the volatiles were removed in vacuo to give a yellowish solid (27.8 g, 87% yield). This was carried onto the next step without further purification. $R_f$ 0.33 (ethyl acetate/hexane 1:9); m.p. 99–100° C.; ¹H NMR (300 MHz, CDCl₃) δ 4.86 (dd, J=3.6, 5.9, 1H), 4.35–4.38 (m, 1H), 2.90 (m, 1H), 2.63–2.73 (m, 1H), 2.49–2.52 (m, 1H), 2.20–2.36 (m, 2H), 1.95–2.00 (m, 1H). 1.38 (d, J=7.2, 3H); ¹³C NMR (75 MHz, CDCl₃) δ 178.2, 81.6, 43.8, 34.3, 29.3, 27.8, 19.5, 19.1; MS (EI) m/z 266 (M⁺, 4), 139 ([M-I]⁺, 80), 95 (100), 79 (16), 67 (26), 55 (29); $[\alpha]_D$–3.60° (c=2.22, CHCl₃).

(1R,2R,5R)-2-methyl-6-oxabicyclo[3.2.1]octan-7-one (9) (Avery, J. W., et al., Tetrahedron Lett., 35: 9337–9338 (1994)). A solution of 8 (26.8 g, 101 mmol), tributyltin hydride (29.8 mL, 111 mmol), and AIBN (200 mg) in benzene (300 mL) was refluxed overnight. After removing the benzene solvent in vacuo, diethyl ether (250 mL) and 10% aqueous KF (250 mL) was added. Stirring for 30 min precipitated a tributyltin flouride polymer. The polymer was filtered and the mother liquors were extracted with methylene chloride (3×100 mL). The combined organics were dried (MgSO₄) and the volatiles were removed in vacuo to yield an oil which was purified by flash chromatography to give a yellowish solid (13.2 g, 94% yield). $R_f$ 0.26 (ethyl acetate/ hexane 1:9); m.p. 62–63° C.; ¹H NMR (300 MHz, CDCl₃) δ 4.76–4.80 (m, 1H), 2.43–2.46 (m, 1H), 2.12–2.25 (m, 2H), 2.01–2.05 (m, 1H), 1.89–1.98 (m, 2H), 1.62–1.70 (m, 1H), 1.41–1.47 (m, 1H), 1.13 (d, J=6.8, 3H); ¹³C NMR (75 MHz, CDCl₃) δ 179.1, 78.1, 44.5, 31.0, 28.1, 24.8, 24.4, 17.5; MS (EI) m/z 140 (M⁺, 3), 112 ([M-CO]⁺, 3), 97 (28), 81(100), 70 (38), 55 (48); $[\alpha]_D$+31.3 (c=0.96°, CHCl₃); Analysis calc'd for C₈H₁₂O₂: C, 68.54; H, 8.63. Found: C, 68.15; H, 8.60.

Ethyl (1R,2R,5R)-5hydroxy-2-methylcyclohexane-1-carboxylate (10). To anhydrous ethanol (250 mL) at room temperature was added sodium metal (5.0 g, 0.217 mol). After dissolution of the sodium metal (which produces sodium ethoxide in the reaction medium), 9 (13.2 g, 94.3 mmol) was added and allowed to stir at room temperature for one hour, whereupon the reaction was complete by TLC. The mixture was quenched by addition to saturated ammonium chloride (300 mL), and extracted with methylene chloride (3×100 mL). The combined organics were dried (MgSO₄) and the volatiles were removed in vacuo to give an oil (17.3 g, 99% yield). This was carried onto the next step without further purification. $R_f$ 0.25 (ethyl acetate/hexane 3:7); ¹H NMR (300 MHz, CDCl₃) δ 4.11 (q, J=7.2, 2H), 3.52–3.61 (m, 1H), 1.92–2.08 (m, 4H), 1.69–1.78 (m, 1H), 1.56–1.69 (m, 1H), 1.39–1.50 (m, 1H), 1.26–1.36 (m, 1H), 1.23 (t, J=7.2, 3H), 0.97–1.11 (m, 1H), 0.86 (d, J=6.4, 3H); ¹³C NMR (75 MHz, CDCl₃) δ 174.9, 69.8, 60.2, 49.7, 38.2, 35.0, 33.6, 32.4, 19.6, 14.2; MS (EI) m/z 186 (M⁺, 3), 168 ([M-H₂O]⁺, 57), 141 ([M-OCH₂CH₃]⁺, 16), 129 (29), 95 (100), 73 (21), 55 (30); $[\alpha]_D$–26.6° C.=1.10, CH₂Cl₂). Analysis calc'd for C₁₀H₁₈O₃: C, 64.49; H, 9.74. Found: C, 64.68; H, 9.51.

Ethyl (1R,2R)-2-methylcyclohexane-5-one1-carboxylate (11). To a suspension of pyridinium chlorochromate (36.0 g, 167 mmol) in methylene chloride (200 mL) was added 10 (17.27 g, 92.8 mmol), whereupon the mixture became a dark homogenous solution. The reaction was stirred overnight. Diethyl ether (3×300 mL) was added and the product was passed through a short column of florisil to remove the chromium salts. Removal of the solvent in vacuo gave an oil (15.9 g, 93% yield). This was carried onto the next step without further purification. $R_f$ 0.61 (ethyl acetate/hexane 3:7); ¹H NMR (300 MHz, CDCl₃) δ 4.18 (dq, J=1.1, 7.2, 2H), 2.35–2.63 (m, 5H), 2.01–2.19 (m, 2H), 1.42–1.53 (m, 1H), 1.28 (t, J=7.2, 3H), 1.03 (d, J=6.4, 3H); ¹³C NMR (75 MHz, CDCl₃) δ 208.9, 173.5, 60.6, 50.5, 42.7, 40.3, 33.4, 33.2, 19.0, 14.1; MS (EI) m/z 184 (M⁺, 23), 169 ([M-CH₃]⁺, 3), 155 ([M-CH₂CH₃]⁺, 8), 139 ([M-OCH₂CH₃]⁺, 8), 128 (35), 111 (100), 99 (46). 55 (50); $[\alpha]_D$–46.9° (c=1.00, CH₂Cl₂). Analysis calc'd for C₁₀H₁₆O₃: C, 65.19; H, 8.75. Found: C, 65.06; H, 8.73.

Ethyl (1R,2R,5S)-5-hydroxy-2-methylcyclohexane-1-carboxylate (12). To a cold (–78° C.) solution of 11 (14.9 g, 80.8 mmol) in THF (250 mL) was added K-Selectride (potassium tri-sec-butylborohydride) (95.0 mmol, 1.0 M in THF). After addition was complete, the mixture was allowed to warm to –50° C. and stirred for an additional 4 h, whereupon the reaction was complete by TLC. The reaction was quenched by addition to 2.2 M NaH₂PO₄/K₂HPO₄ buffer (300 mL, pH =7). This was cooled (0° C.) and 30% hydrogen peroxide (42 mL, 370 mmol) was added and the mixture was allowed to stir overnight. The layers were separated and the aqueous layer was extracted with ethyl acetate (4×200 mL). The combined organics were washed with brine (300 mL), 1.0 M sodium sulfite (300 mL), dried (MgSO₄) and the volatiles were removed in vacuo to yield an oil which was further purified by flash chromatography (12.48 g, 83% yield). $R_f$ 0.35 (ethyl acetate/hexane 3:7); ¹H NMR (300 MHz, CDCl₃) δ 4.45–4.54 (m, 1H), 4.10 (q, J=7.2, 2H), 2.34–2.44 (m, 1H), 2.00–2.30 (b, 1H), 1.26–1.91 (m, 7H), 1.22 (t, J=7.2, 3H), 0.89 (d, J=6.4, 3H); ¹³C NMR (75 MHz, CDCl₃) δ 176.1, 65.4, 60.0, 45.1, 35.8, 33.9, 32.0, 27.6, 20.2, 14.2; MS (EI) m/z 186 (M⁺, 3), 168 ([M-H₂O]⁺, 37), 141 ([M-OCH₂CH₃]⁺, 25), 130 (12), 95 (100), 73 (27), 55 (34); $[\alpha]_D$–27.4° (c=1.10, CH₂Cl₂). Analysis calcs'd for C₁₀H₁₈O₃: C, 64.49; H, 9.74. Found: C, 64.19; H, 9.62.

Ethyl (1R,2R,5R)-5-iodo-2-methylcyclohexane-1-carboxylate (4a). To a cold (0° C.). solution of 12 (8.28 g, 44.5 mmol) in 1:2 methylene chloride/carbon tetrachloride (400 mL) was added triphenylphosphine (14.0 g, 53.4 mmol), imidazole (3.63 g, 53.4 mmol), and iodine (13.5 g, 54.4 mmol). The reaction mixture was allowed to warm to room temperature and stirred overnight. The reaction was quenched by addition of saturated sodium thiosulfate (300 mL) and stirred until the solution became clear. The layers were separated and the aqueous layer was extracted with methylene chloride (2×200 mL). The combined organics were washed with sodium thiosulfate (200 mL), brine (200 mL), dried (Na₂SO₄) and the volatiles were removed in vacuo to yield a solid which was purified by flash chromatography to give a oil (7.0 g, 53% yield). Analysis on a 60 m SPB-608 column (DeMilo, A. B., et al., J. Chromatography A, 673: 295–298 (1994)) indicated production of 4a in high diastereoselectvity (>40:1), thus indicating that the other 14 regio- and stereoisomers are present at a 40 fold lower concentration than 4a. $R_f$ 0.76 (ethyl acetate/hexane 3:7); ¹H NMR (300 MHz, CDCl₃) δ 4.13 (q, J=7.2, 2H), 4.00–4.09 (m, 1H), 2.51–2.58 (m, 1H), 2.37–2.45 (m, 1H), 2.10–2.22 (m, 1H), 1.95–2.09 (m, 2H), 1.69–1.80 (m, 1H), 1.59–1.67 (m, 1H), 1.26 (t, J=7.2, 3H), 1.06–1.12 (m, 1H), 0.86 (d, J=6.4, 3H); ¹³C NMR (75 MHz, CDCl₃) δ 173.4, 60.4, 53.3, 42.7, 39.9, 36.2, 33.1, 25.8, 20.0, 14.2; MS (EI) m/z 251 ([M-OCH₂CH₃]⁺, 2), 169 ([M-I]⁺, 21), 123 (11), 95 (100), 81 (8), 67 (14), 55 (17); $[\alpha]_D$–29.0° (c=0.72, CH₂Cl₂).

Ethyl(1S, 2S, 5S)-5-iodo-2-methylcyclohexane-1-carboxylate (4b) was produced in an analogous manner from the oxazolidinone derived from L-phe. $[\alpha]_D$+28.8° (c=0.65, $CH_2Cl_2$).2

Ethyl(1SR,2SR,5SR)-5-iodo-2-methylcyclohexane-1-carboxylate (4) was generated in an analogous manner from racemic (1RS, 6RS)-6-methyl-3-cyclohexene-1-carboxylic acid.

As shown above, a convenient stereoselective synthesis of the enantiomers of CER $B_1$ (4) has been described. The synthesis was accomplished in 15% overall yield and is amenable to large scale production.

Field attraction of Mediterranean fruit fly, Ceratitis capitata (Wiedemann), to stereoselectively synthesized enantiomers of the ceralure B1 isomer: The attractancy of the two newly synthesized ceralure B1 enantiomers was evaluated against laboratory and wild populations of medfly and the response to these compounds was compared to commercially available trimedlure and ceralure. Field tests using released sterile flies on the island of Hawaii or field tests against wild populations of medfly in commercial coffee plantations on the island of Kauai were carried out to compare the attractancy, dose response and initial persistence of the new molecules and a racemic (50:50) mixture of the two.

Test compounds: Liquid trimedlure (UOP Chemicals, East Rutherford, N.J.) (98% pure; density 1.02 g/ml) and ceralure (Agrisense/Biosys, Palo Alto, Calif.) (98% pure; density 1.43 g.ml) were purchased from commercial sources. The 2 g polymeric plug (Agrisense/Biosys, Palo Alto, Calif.) was the same product used by action agencies such as USDA-APHIS and California Department of Food and Agriculture (CDFA) in their surveillance and detection programs against medfly. The enantiomers of ceralure B1 (ethyl-cis-5-iodo-trans-2-methylcyclohexane-1-carboxylate) (henceforth referred to as the 1R,2R,5R and 1S,2S,5S enantiomers respectively) were synthesized using the 9 step process (described above) which yielded both enantiomers with high purity (97% ) and an overall yield of 15%. The racemic mixture of the two enantiomers was produced starting from racemic (5), which is (1RS, 6RS)-6-methyl-3-cyclohexene-1-carboxylic acid, using the above described process used to produce ethyl (1R,2R,5R)-5-iodo-2-methylcyclohexane-1-carboxylate (4a).

Insects: Sterilized Mediterranean fruit fly pupae were obtained from the USDA-ARS-USPBARC rearing facility in Honolulu, Hi. The flies were reared on an artificial diet (Tanaka, N., et al., J. Econ. Entomol., 62: 967–968 (1969)) under standard mass-rearing conditions and sterilized as pupae at a dose of 150 GY and two days before emergence. Flies were shipped by air to Hilo where 150 ml of pupae (both sexes) was placed in 15-gallon Rubbermaid action packers modified by screened panels on the bottoms and sides of the units. The emerged flies were given water, sugar and hydrolyzed yeast protein. Flies were 2–9 days old when tested. Wild populations of medflies were present in coffee orchards on the island of Kauai.

Bioassays: All tests were conducted using tent-shaped Jackson traps with open ends, a removable sticky insert and a ½ inch cotton wick containing the test chemical (Harris, E. J., et al., J. Econ. Entomol., 64: 62–65 (1971)). All tests were conducted using a randomized complete block design having five traps of each treatment in the block. The tests were replicated at least 5 times.

Dose-response tests: 10 mg, 1 mg, 0.1 mg and 0.01 mg doses of each compound (in 100 µl acetone) were tested on ½ inch cotton wicks in Jackson traps. Acetone was used in the control. The treatments were ceralure B1 (1S,2S,5S), ceralure B1 (Racemic), ceralure B1 (1R,2R,5R), trimedlure, ceralure and a blank control. Traps were placed in a macadamia nut orchard on the island of Hawaii near the town of Hilo. Traps were separated by every other tree in every row (approximately 15 meters between traps). Flies (approximately 6,000) were then released by slowly walking between rows while allowing the flies to escape from the opened action packer. Traps were left out for 48 hours after which the traps were collected and brought back to the lab for analysis. Both males and females were counted on the sticky inserts.

Longevity tests: Preliminary tests to determine the effectiveness of the different chemical compounds over time were also carried out using sterile flies released in a macadamia nut orchard. In these tests all compounds were applied to the cotton wick at a 10 mg dose. 100 µl of each compound was placed on a ½ inch wick inside a Jackson trap. Traps were serviced weekly for three weeks. Inserts were changed each week and new flies were released but the same compounds were left in the field to age.

Wild fly response to ceralure B1 enantiomers: An open field test was conducted at Kauai Coffee in Koloa, Kauai to determine if the lures were attractive against wild medflies. The first experiment on Kauai compared test compounds at the 10 mg dose with trimedlure. Traps were set out in a randomized complete block design and serviced every two days as in the first test with laboratory reared sterile flies. In a second experiment the test compounds at the 10 mg dose were compared against a standard 2 g trimedlure plug. These traps were serviced on the second and seventh day after being placed in the field. All compounds were tested in Jackson traps. Traps were placed in two different field plots in a randomized complete block design. There were five replicates. Male and female trap captures were recorded.

Data analysis: Both male and female medfly were counted on the sticky inserts. However, since the trap captures were overwhelmingly male biased, only data from male captures are included in the analysis. Data was subjected to analysis of variance (Proc GLM) and the Turkey's test for separation of means values. Significant differences in response were determined at the P=0.05 level. Data were not transformed prior to analysis. Statistical analysis was performed on SAS ver 6.12 (SAS Institute, Cary, N.C.) using a PC. Values presented on the tables are mean values SEM.

Results

Figure 2:
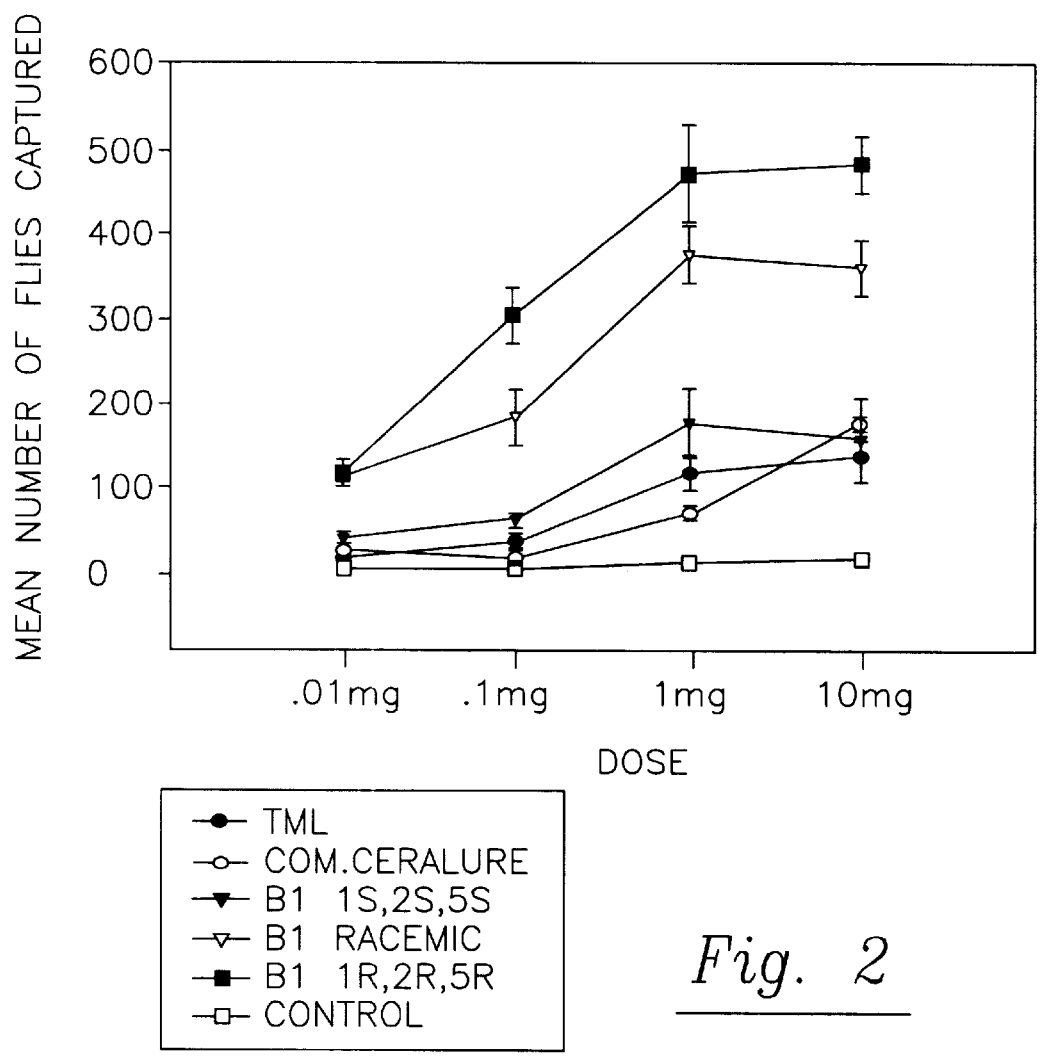
FIG. 2 shows the dosage response test of ceralure compounds with sterile released medflies.

B1 racemic mixture (50:50) and B1 (1R,2R,5R) captured significantly more male medflies than B1 (1S,2S,5S), commercial trimedlure, commercial ceralure and (acetone) control at the 10 mg, 1 mg, 0.1 mg and 0.01 mg dosages (Table 1). At the 10 mg, 1 mg, and 0.1 mg doses, B1 (1R,2R,5R) captured significantly more males than the B1 racemic mixture (FIG. 2).

In longevity studies, after one week, B1 (1R,2R,5R) and the B1 racemic mixture captured significantly more males than B1 (1S,2S,5S), commercial trimedlure, commercial ceralure and control (Table 2). After two weeks, the B1 racemic mixture captured significantly more males than any other compound. The overall trap captures were low compared to the first week. By the third week of testing, the compounds were capturing very few male medflies. All compounds were tested at the 10 mg dose.

In wild populations of medflies, B1 (1R,2R,5R) captured significantly more males than the B1 racemic mixture, which had significantly higher captures than the B1 (1S,2S, 5S) and commercial ceralure, which was significantly higher than from commercial trimedlure and control (Table 3a). All compounds were tested at the 10 mg dosage.

In a separate experiment the standard 2 g trimedlure plug was compared with B1 (1R,2R,5R), B1 racemic and B1 (1S,2S,5S) at the 10 mg dose. After 48 hours trap captures were recorded. B1 (1R,2R,5R) captured the most male medflies but not significantly more than the B1 racemic mixture and commercial trimedlure, but still significantly more than B1 (1S,2S,5S), acetone control and control blank (Table 3b). After 7 days of weathering treatments, trimedlure plugs captured significantly more males (5 day capture) than B1 (1R,2R,5R) and the B1 racemic mixture, which was significantly different from B1 (1S,2S,5S), acetone and control blank.

The above results clearly show that the 1R,2R,5R enantiomer of ceralure B1 is significantly more attractive than its enantiomeric counterpart (1S,2S,5S) or either of the commercial products trimedlure or ceralure (each a mixture of 16 regio and stereoisomers). These results confirm previously published studies (Leonhardt, B. A., et al, J. Entomol. Sci., 31(2): 183–190 (1996); Avery, J. W., et al., J. Entomol. Sci. 29 (4): 543–556 (1994) that the B1 isomer of ceralure is the most attractive of the 8 stereoisomers. The results further refine the information on attraction of the B1 isomer by demonstrating that one of the two enantiomers of the B1 isomer (1R,2R,5R) confers most of the activity while the other (1S,2S,5S) has significantly less activity.

While the results of this study show increased activity for the B1 (1R,2R,5R) enantiomer of the order of 7–10 times that of trimedlure when similar doses are compared, if equal activity using the mean values from Table 1 are compared then it can be seen that trimedlure at the 10 mg dose captured a mean of 133 flies while the 0.01 mg dose of the B1 racemic or the 1R,2R,5R enantiomer alone caught means of 111 and 117 flies respectively. This equates to a dose of 1000 times less 1R,2R,5R enantiomer compared to trimedlure to achieve the same trap capture. Tests on attraction of wild flies using the standard polymeric plug containing 2 g of trimedlure compared to the B1 (1R,2R,5R) enantiomer or the B1 racemic mixture resulted in higher (but not significantly different) trap capture after 2 days despite the 200 fold lower dose of B1 (1R,2R,5R) enantiomer compared to the polymer plug. Some of this difference however can be attributed to the longer life and slower release rate of the trimedlure from the plug which is reflected in the higher trap capture in the trimedlure trap after an additional 5 day trapping period without further recharging of the traps. In addition it is well known in the literature that ceralure is less volatile than trimedlure, which Avery et al. (1994) suggested may be responsible for its greater persistence in the field. Given this information, it is expected that the 1R,2R,5R enantiomer of ceralure B1 will have significantly more activity on a molecule to molecule basis than trimedlure.

In summary, stereoselectively synthesized enantiomers of the ceralure B1 isomer, a potent male lure for male Mediterranean fruit flies, were tested in the field against both laboratory-reared and wild flies in two locations. The B1 (1R,2R,5R) enantiomer was significantly more attractive to both laboratory and wild flies than the B1 (1S,2S,5S) enantiomer which was not significantly different than either commercial trimedlure or ceralure when applied to cotton wicks at equal doses in Jackson traps. The racemic mixture caught more flies than the B1 (1S,2S,5S) enantiomer but was less attractive than the 1R,2R,5R configuration. Dose response studies of the above compounds showed a consistently 7–10 times greater capture of males to the B1 (1R, 2R,5R) enantiomer of ceralure B1 compared to trimedlure, a more volatile compound. Over a three week period, both the racemic mixture of the two enantiomers and the B1 (1R,2R,5R) enantiomer alone caught more flies than the other test compounds, especially after one week. When compared with the standard (2 g) TML plug used in detection programs in California, 10 mg of the B1 (1R,2R,5R) enantiomer of ceralure B1 caught more wild flies after two days than the TML plug. After an additional 5 days the B1 (1R,2R,5R) enantiomer was still capturing approximately 33% of the flies captured in the TML plug baited trap.

The following U.S. Patents are incorporated by reference in their entirety: U.S. Pat. Nos. 5,939,062; 5,907,923; 5,766, 617; 4,891,217; 4,764,366; 4,761,280; 4,152,422; and 3,016,329.

All of the references cited herein are incorporated by reference in their entirety.

Thus, in view of the above, the present invention concerns (in part) the following:

A method of attracting the Mediterranean fruit fly, comprising subjecting the Mediterranean fruit fly to an attractant, wherein said attractant comprises ethyl (1R,2R, 5R)-5-iodo-2-methylcyclohexane-1-carboxylate in an enantomeric excess of at least 70%.

The above method, wherein said ethyl (1R,2R,5R)-5-iodo-2-methylcyclohexane-1-carboxylate has a regio- and diastereochemical purity of >5:1.

The above method, wherein said ethyl (1R,2R,SR)-5-iodo-2-methylcyclohexane-1-carboxylate has a regio- and diastereochemical purity of >10:1.

The above method, wherein said ethyl (1R,2R,5R)-5-iodo-2-methylcyclohexane-1-carboxylate has a regio- and diastereochemical purity of >15:1.

The above method, wherein said ethyl (1R,2R,5R)-5-iodo-2-methylcyclohexane-1-carboxylate has a regio- and diastereochemical purity of >40:1.

The above method, wherein said enantomeric excess is at least 80%.

The above method, wherein said enantomeric excess is at least 90%.

The above method, wherein said enantomeric excess is at least 95%.

The above method, wherein said enantomeric excess is at least 97%.

The above method, wherein said attractant consists essentially of ethyl (1R,2R,5R)-5-iodo-2-methylcyclohexane-1-carboxylate.

The above method, wherein said attractant consists of ethyl (1R,2R,5R)-5-iodo-2-methylcyclohexane-1-carboxylate.

Ethyl (1R,2R,5R)-5-iodo-2-methylcyclohexane-1-carboxylate in an enantomeric excess of at least 70%.

The above compound, wherein said ethyl (1R,2R,5R)-5-iodo-2-methylcyclohexane-1-carboxylate has a regio- and diastereochemical purity of >5:1.

The above compound, wherein said regio- and diastereochemical purity is >10:1.

The above compound, wherein said regio- and diastereochemical purity is >15:1.

The above compound, wherein said regio- and diastereochemical purity is >40:1.

The above compound, wherein said enantomeric excess is at least 80%.

The above compound, wherein said enantiomeric excess is at least 90%.

The above compound, wherein said enantiomeric excess is at least 95%.

The above compound, wherein said enantiomeric excess is at least 97%.

A composition for attracting the Mediterranean fruit fly, comprising ethyl (1R,2R,5R)-5-iodo-2-methylcyclohexane-1-carboxylate in an enantiomeric excess of at least 70%.

The above composition, wherein said ethyl (1R,2R,5R)-5-iodo-2-methylcyclohexane-1-carboxylate has a regio- and diastereochemical purity of >5:1.

The above composition, wherein said regio- and diastereochemical purity is >10:1.

The above composition, wherein said regio- and diastereochemical purity is >15:1.

The above composition, wherein said regio- and diastereochemical purity is >40:1.

The above composition, wherein said enantiomeric excess is at least 80%.

The above composition, wherein said enantiomeric excess is at least 90%.

The above composition, wherein said enantiomeric excess is at least 95%.

The above composition, wherein said enantiomeric excess is at least 97%.

The above composition, further comprising an inert carrier for said ethyl (1R,2R,5R)-5-iodo-2-methylcyclohexane-1-carboxylate.

The above composition, further comprising a Mediterranean fruit fly control agent.

The above composition, wherein said Mediterranean fruit fly control agent is an insecticide.

The above composition, consisting essentially of ethyl (1R,2R,5R)-5-iodo-2-methylcyclohexane-1-carboxylate, an inert carrier, and optionally a Mediterranean fruit fly control agent.

The above composition, consisting of ethyl (1R,2R,5R)-5-iodo-2-methylcyclohexane-1-carboxylate, an inert carrier, and optionally a Mediterranean fruit fly control agent.

A method of making ethyl (1R,2R,5R)-5-iodo-2-methylcyclohexane-1-carboxylate in an enantiomeric excess of at least 70%, comprising reacting ethyl (1R,2R,5S)-5-hydroxy-2-methylcyclohexane-1-carboxylate (12) with $Ph_3P$-imidazole-$I_2$ (or $Ph_3P$-2,6-lutidine-$I_2$) in a carbon tetrachloride/methlylene chloride mixture to produce ethyl (1R,2R,5R)-5-iodo-2-methylcyclohexane-1-carboxylate (4a).

The above method, wherein said ethyl (1R,2R,5R)-5-iodo-2-methylcyclohexane-1-carboxylate has a regio- and diastereochemical purity of >5:1.

The above method, wherein said regio- and diastereochemical purity is >10:1.

The above method, wherein said regio- and diastereochemical purity is >15:1.

The above method, wherein said regio- and diastereochemical purity is >40:1.

The above method, wherein said enantiomeric excess is at least 80%.

The above method, wherein said enantiomeric excess is at least 90%.

The above method, wherein said enantiomeric excess is at least 95%.

The above method, wherein said enantiomeric excess is at least 97%.

The above method, further comprising reacting ethyl (1R,2R)-2-methylcyclohexane-5-one-1-carboxylate (11) with K-Selectride (potassium tri-sec-butylborohydride) in THF at −78° C. to produce said ethyl (1R,2R,5S)-5-hydroxy-2-methylcyclohexane-1-carboxylate (12).

The above method, further comprising reacting (1R,2R,5R)-ethyl-5-hydroxy-2-methylcyclohexane-1-carboxylate (10) with pyridinium chlorochromate in methylene chloride to produce said ethyl (1,2R)-2-methylcyclohexane-5-one-1-carboxylate (11).

The above method, further comprising reacting (1R,2R,5R)-2-methyl-6-oxabicyclo[3.2.1]octan-7-one (9) with EtONa and ethanol, or with Na and ethanol to produce said (1R,2R,5R)-ethyl-5-hydroxy-2-methylcyclohexane-1-carboxylate (10).

The above method, further comprising reacting (1R,2R,4S, 5S)-4-iodo-2-methyl-6-oxabicyclo[3.2.1]octan-7-one (8) with n-$Bu_3SnH$ and catalytic AIBN in refluxing benzene, or with Raney Nickel in the presence of pyridine under 50 psi $H_2$, to produce said (1R,2R,5R)-2-methyl-6-oxabicyclo [3.2.1]octan-7-one (9).

The above method, further comprising reacting (1R,6R)-6-methyl-3-cyclohexene-1-carboxylic acid (5) with $I_2$, KI and $NaHCO_3$ and methylene chloride to produce said (1R, 2R,4S, 5S)-4-iodo-2-methyl-6-oxabicyclo[3.2.1 ]octan-7-one (8).

The above method, further comprising reacting (4R)-3-((4'R,5'R)-cyclohexene-4'-carbonyl)-4-(phenylmethyl)-2-oxazolidinone (7) with lithium hydroperoxide in THF/$H_2O$ to produce said (1R,6R)-6-methyl-3-cyclohexene-1-carboxylic acid (5).

The above method, further comprising reacting (4R)-3-((E)-2-butenoyl)-4-(phenylmethyl)-2-oxazolidinone (6) with butadiene in the presence of 2 equivalents of Et2AlCl at −15° C. to produce said (4R)-3-((4'R,5'R)-cyclohexene-4'-carbonyl)-4-(henylmethyl-2-oxazolidione (7).

The above method, further comprising reacting (R)-4-(phenylmethyl)-2-oxazolidinone (5) with n-butyllithium and (E)-crotonyl chloride to produce said (4R)-3-((E)-2-butenoyl)-4-(phenylmethyl)-2-oxazolidinone (6).

A method of making ethyl (1R,2R,5R)-5-iodo-2-methylcyclohexane-1-carboxylate in an enantiomeric excess of at least 70%, comprising reacting (R)-4-(phenylmethyl)-2-oxazolidinone (5) with n-butyllithium and (E)-crotonyl chloride to produce (4R)-3-((E)-2-butenoyl)-4-(phenylmethyl)-2-oxazolidinone (6), reacting said (4R)-3-((E)-2-butenoyl)-4-(phenylmethyl)-2-oxazolidinone (6) with butadiene in the presence of 2 equivalents of Et2AlCl at −15° C. to produce (4R)-3-((4'R,5'R)-cyclohexene-4-carbonyl)-4-(phenylmethyl)-2-oxazolidinone (7), reacting said (4R)-3-((4'R,5'R)-cyclohexene-4'-carbonyl)-4-(phenylmethyl)-2-oxazolidinone (7) with lithium hydroperoxide in THF/$H_2O$ to produce (1R, 6R)-6-methyl-3-cyclohexene-1-carboxylic acid (5), reacting said (1R,6R)-6-methyl-3-cyclohexene-1-carboxylic acid (5) with $I_2$, KI and $NaHCO_3$ in methylene chloride to produce (1R,2R,4S,5s)4-iodo-2-methyl-6-oxabicyclo[3.2.1]octan-7-one (8), reacting said (1R,2R,4S,5S)-4-iodo-2-methyl-6-oxabicyclo[3.2.1]octan-7-one (8) with n-Bu$_3$SnH and catalytic AIBN in refluxing benzene, or with Raney Nickel in the presence of pyridine under 50 psi H$_2$, to produce (1R,2R,5R)-2-methyl-6-oxabicyclo[3.2.1] octan-7-one (9), reacting said (1R,2R,5R)-2-methyl-6-oxabicyclo[3.2.1] octan-7-one (9) with with EtONa and ethanol, or with Na and ethanol to produce ethyl (1R,2R,5R)-5-hydroxy-2-methylcyclohexane-1-carboxylate (10), reacting said ethyl (1R,2R,5R)-5-hydroxy-2-methylcyclohexane-1-carboxylate (10) with pyridinium chlorochromate in methylene chloride to produce ethyl(1R,2R)-2-methylcyclohexane-5-one-1-carboxylate (11), reacting said ethyl (1R,2R)-2-methylcyclohexane-5-one-1-carboxylate (11) with K-Selectride (potassium tri-sec-butylborohydride) in THF at −78° C. to produce ethyl (1R,2R,5S)-5-hydroxy-2-methylcyclohexane-1-carboxylate (12), and reacting said ethyl (1R,2R,5S)-5-hydroxy-2-methylcyclohexane-1-carboxylate (12) with Ph$_3$P-imidazole-I$_2$ (or Ph$_3$P-2,6-lutidine-I$_2$) in a carbon tetrachloride/methylene chloride mixture to produce ethyl (1R,2R,5R)-5-iodo-2-methylcyclohexane-1-carboxylate (4a).

The above method, wherein said ethyl (1R,2R,5R)-5-iodo-2-methylcyclohexane-1-carboxylate has a regio- and diastereochemical purity of >5:1.

The above method, wherein said regio- and diastereochemical purity is >10:1.

The above method, wherein said regio- and diastereochemical purity is >15:1.

The above method, wherein said regio- and diastereochemical purity is >40:1.

The above method, wherein said enantomeric excess is at least 80%.

The above method, wherein said enantomeric excess is at least 90%.

The above method, wherein said enantomeric excess is at least 95%.

The above method, wherein said enantomeric excess is at least 97%.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 2

Response of released Mediterranean fruit flies to ceralure compounds over a three week test period.

| | | Week 1 | Week 2 | Week 3 |
|---|---|---|---|---|
| A. TML | 15 | 111 ± 19.4 bc | .06 ± .06 b | 0 ± 0 a |
| B. Com. Ceralure | 15 | 135 ± 16.8 b | 3.1 ± 2.2 b | .47 ± .27 a |
| C. B1 1S,2S,5S | 15 | 135.7 ± 33.4 b | 5.5 ± 4.5 b | 0 ± 0 a |
| D. B1 Racemic | 15 | 274.5 ± 21.8 a | 79.6 ± 33.3 a | 4.7 ± 3.7 a |
| E. B1 1R,2R,5R | 15 | 338.9 ± 40.1 a | 69.3 ± 24.9 ab | .3 ± .3 a |
| F. Control | 15 | 11.4 ± 3.9 c | 2.3 ± 2.1 b | .07 ± .07 a |

Data analyzed by Proc GLM; means followed by same letter in a column are not significantly different (P > 0.05) by Tukey's test.

TABLE 3a

Response of wild Mediterranean fruit flies to 10 mg of ceralure compounds.

| Treatment | N | Mean ± s.e. |
|---|---|---|
| A. TML | 50 | 14.1 ± 2.2 cd |
| B. Com. Ceralure | 50 | 31.8 ± 4.4 c |
| C. B1 1S,2S,5S | 50 | 40.5 ± 8.3 c |
| D. B1 Racemic | 50 | 70.8 ± 10 b |
| E. B1 1R,2R,5R | 50 | 104.2 ± 13.7 a |
| F. control | 50 | 3 ± .1 d |

TABLE 3b

Response of wild Mediterranean fruit flies to 2 g TML plug vs 10 mg of ceralure compounds.

| Treatment | N | 2days | 7days |
|---|---|---|---|
| A. TML plug | 40 | 79.9 ± 17.3 ab | 149.3 ± 20.3 a |
| B. B1 1S,2S,5S | 40 | 35.4 ± 5.8 bc | 10.8 ± 2.6 c |
| C. B1 Racemic | 40 | 83.9 ± 17.5 ab | 37.9 ± 8.0 bc |
| D. B1 1R,2R,5R | 40 | 117.1 ± 22.6 a | 50.9 ± 10.5 b |
| E. Acetone control | 40 | 1 ± .3 c | .32 ± .18 c |
| F. Blank control | 40 | 0.5 ± 0.1 c | .15 ± .06 c |

Data analyzed by Proc GLM; means followed by same letter in a column are not significantly different (P > 0.05) by Tukey's test.

We claim:

1. A method of attracting the Mediterranean fruit fly, comprising subjecting the Mediterranean fruit fly to an attractant, wherein said attractant comprises ethyl (1R,2R,5R)-5-iodo-2-methylcyclohexane-1-carboxylate in an enantomeric excess of at least 70%.

TABLE 1

Response of released Mediterranean fruit flies to different dosages of ceralure compounds.

| | | Dose | | | |
|---|---|---|---|---|---|
| | | 10 mg | 1 mg | .1 mg | *.01 mg |
| Treatment | N | Mean male fly capture ± s.e. | | | |
| A. TML | 15 | 133.27 ± 30.7 c | 112.53 ± 20.9 bc | 31.07 ± 12.4 c | 14 ± 3.4 bc |
| B. Com. Ceralure | 15 | 170.47 ± 33.1 c | 65.07 ± 9.5 bc | 11.27 ± 4.1 c | 23.4 ± 6.3 bc |
| C. B1 1S,2S,5S | 15 | 151.80 ± 25.3 c | 173 ± 42.2 b | 57.20 ± 8.3 c | 38.3 ± 6.5 b |
| D. B1 Racemic | 15 | 365.53 ± 33.7 b | 376.8 ± 36.7 a | 179.67 ± 33.5 b | 111 ± 12.2 a |
| E. B1 1R,2R,5R | 15 | 487.27 ± 33 a | 473.07 ± 56.6 a | 303.07 ± 34.5 a | 117 ± 14.1 a |
| F. Control | 15 | 11.3 ± 3 d | 8.4 ± 2.7 d | 2.07 ± .7 c | 2.3 ± 1 c |

Data analyzed by Proc GLM; means followed by same letter in a column are not significantly different (P > 0.05) by Tukey's test.
*.01 mg dose had N = 25 replicates.

2. The method according to claim 1, wherein said ethyl (1R,2R,5R)-5-iodo-2-methyl-1-carboxylate has a regio- and diastereochemical purity of >5:1.

3. The method according to claim 1, wherein said ethyl (1R,2R,5R)-5-iodo-2-methyl-1-carboxylate has a regio- and diastereochemical purity of >10:1.

4. The method according to claim 1, wherein said ethyl (1R,2R,5R)-5-iodo-2-methyl-1-carboxylate has a regio- and diastereochemical purity of >15:1.

5. The method according to claim 1, wherein said ethyl (1R,2R,5R)-5-iodo-2, methyl-1-carboxylate has a regio- and diastereochemical purity of >40:1.

6. The method according to claim 1, wherein said enantomeric excess is at least 80%.

7. The method according to claim 1, wherein said enantomeric excess is at least 90%.

8. The method according to claim 1, wherein said enantomeric excess is at least 95%.

9. The method according to claim 1, wherein said enantomeric excess is at least 97%.

10. Ethyl (1R,2R,5R)-5-iodo-2-methylcyclohexane-1-carboxylate in an enantomeric excess of at least 70%.

11. A composition for attracting the Mediterranean fruit fly, comprising ethyl (1R,2R,5R)-5-iodo-2-methylcyclohexane-1-carboxylate in an enantomeric excess of at least 70%.

* * * * *